US008587650B2

(12) United States Patent
Ruuska

(10) Patent No.: US 8,587,650 B2
(45) Date of Patent: Nov. 19, 2013

(54) DEVICE FOR MONITORING A WEB

(75) Inventor: Hannu Ruuska, Muurame (FI)

(73) Assignee: Metso Automation Oy, Vantaa (FI)

( * ) Notice: Subject to any disclaimer, the term of this patent is extended or adjusted under 35 U.S.C. 154(b) by 1191 days.

(21) Appl. No.: 12/223,249

(22) PCT Filed: Feb. 1, 2007

(86) PCT No.: PCT/FI2007/050058
§ 371 (c)(1),
(2), (4) Date: Jul. 24, 2008

(87) PCT Pub. No.: WO2007/088250
PCT Pub. Date: Aug. 9, 2007

(65) Prior Publication Data
US 2010/0214416 A1    Aug. 26, 2010

(30) Foreign Application Priority Data
Feb. 1, 2006    (FI) ...................................... 20065078

(51) Int. Cl.
*H04N 7/18*    (2006.01)
(52) U.S. Cl.
USPC ............................ 348/125; 348/128; 382/141
(58) Field of Classification Search
USPC .................. 348/125, 129–130, 128; 382/141
See application file for complete search history.

(56) References Cited

U.S. PATENT DOCUMENTS

| | | | | |
|---|---|---|---|---|
| 5,305,392 A * | 4/1994 | Longest et al. | ............... | 382/112 |
| 5,359,525 A * | 10/1994 | Weyenberg | ................... | 700/124 |
| 5,440,648 A * | 8/1995 | Roberts et al. | ................ | 382/141 |
| H1616 H * | 12/1996 | Wolfe | .............................. | 348/88 |
| 5,982,452 A * | 11/1999 | Gregson et al. | ............... | 348/584 |
| 6,327,374 B1 * | 12/2001 | Piironen et al. | ............... | 382/108 |
| 6,531,707 B1 * | 3/2003 | Favreau et al. | .......... | 250/559.46 |
| 6,535,621 B1 * | 3/2003 | Fujita | ............................. | 382/112 |
| 7,382,457 B2 * | 6/2008 | Kiraly | ........................... | 356/430 |
| 2003/0038944 A1 | 2/2003 | Hamalainen et al. | | |
| 2005/0139792 A1 * | 6/2005 | Rivera et al. | ............. | 250/559.45 |
| 2005/0226466 A1 | 10/2005 | Seymour | | |
| 2006/0078167 A1 * | 4/2006 | Heikkila et al. | .............. | 382/112 |
| 2007/0008538 A1 * | 1/2007 | Kiraly | ........................... | 356/430 |

FOREIGN PATENT DOCUMENTS

| | | |
|---|---|---|
| EP | 0798886 | 10/1996 |
| EP | 09145638 | 6/1997 |
| EP | 0816825 | 1/1998 |

* cited by examiner

Primary Examiner — Duyen Doan
(74) Attorney, Agent, or Firm — Fildes & Outland, P.C.

(57) ABSTRACT

The invention relates to a device for monitoring a web. The device includes cameras imaging the web in order to take digital images of the web from a transverse area of the web at the imaging frequency. Each camera includes an image element, which consists of pixels. The individual pixels of the imaging element of the camera are real image-elements. The real image-elements are arranged to combine to form effective image-elements of the web in the machine direction. In addition, the cameras used in the device are matrix cameras, the imaging elements in which are arranged to be exposed simultaneously. The real image-elements are arranged to be combined to form effective image-elements by exploiting the binning function of the matrix camera. The device includes a strobe-lighting unit, the synchronization of which is arranged in step with the exposure of the matrix cameras, the imaging periods being common to all the cameras. The imaging frequency is arranged to be such that essentially all the areas of the web are imaged.

17 Claims, 3 Drawing Sheets

DEVICE FOR MONITORING A WEB

Figure 1:
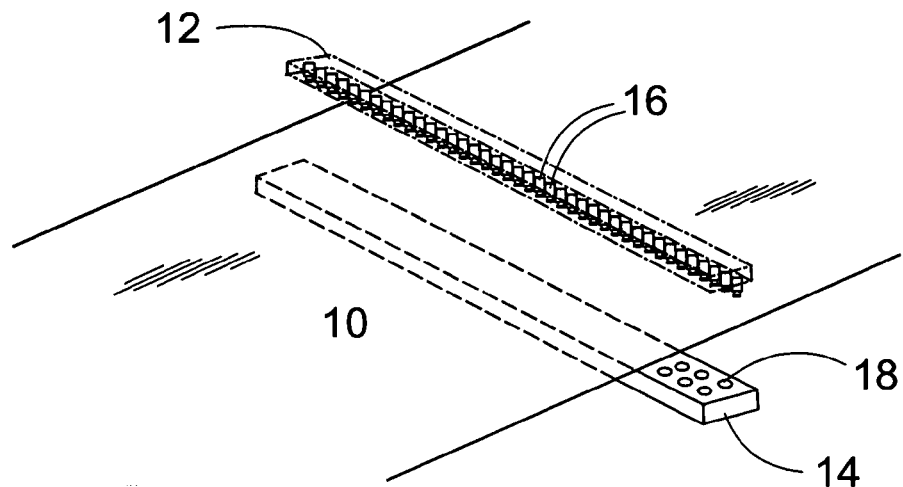

The present invention relates to a device for monitoring a web, which device includes cameras imaging the web in order to take digital images of the web from a transverse area of the web at the imaging frequency, and each camera includes an image element, which consists of pixels, and the individual pixels of the imaging element of the camera are real image-elements, and the real image-elements are arranged to combine to form effective image-elements of the web in the machine direction.

Digital cameras have been used for detecting faults in various types of webs. In patent publication DE19720308, a matrix camera is used in fault detection. The matrix camera is used to locate faults in the web. The detection precision is such that a pixel of the imaging element of the camera corresponds to an area in the web of about 0.75 mm*0.75 mm. When the web is imaged at this precision, rubbish and similar faults are generally detected. The level in question is adequate in many cases, if the paper grade in question is of the sc or newsprint type. However, many webs, particularly coated papers, contain faults that are even smaller than this, such as coating streaks in the longitudinal direction. It would be necessary to see such faults already in the order of magnitude of 0.1 mm.

If the prior art is used to attempt to detect even narrower streaks, a pixel of the camera element should be focussed on an even smaller area. If the intention is for a pixel to correspond to an even smaller area, the number of cameras must be increased, leading to a considerable increase in the bit flow. The increased bit flow requires even larger transfer and calculation capacities. More cameras and greater transfer and calculation capacities are always a cost item. An increasingly accurate image signal will produce micro-formation on the paper. The appearance of paper micro-formation in the images increases the noise appearing in the signal. When a pixel of the camera element corresponds to an even smaller area in the web, less light is collected for the image element, so that the amount of light, i.e. on the other hand the exposure time becomes a problem. This makes detection, according to the prior art, of narrow machine-direction streaks very difficult.

Publication EP 0738886 discloses a coating-density analyser and a method to use an asynchronous TDI-CCD camera. These cameras are generally used in an attempt to amplify the light power in poor lighting conditions. The camera disclosed in the publication is used to image the same physical image-element in each row by phasing the imaging frequency with the movement of the web. If the imaging frequency is not precisely synchronized with the movement of the web, as is the case in some of the publication's examples, the result obtained is an exposure of a lengthened area in the machine direction, the length of which is, according to the publication, only about two times its width. Using the apparatus of the publication, in a typical case an area 12 mm×24 mm on an area 15-cm long is imaged in stages into imaging pixels on the same row, which are finally summed. Thus a TDI-CCD camera does not permit continuous imaging, but instead leaves a completely non-imaged area between the imaging periods.

Publication US 2003/0038944A1 discloses a spectroscopical imaging method, in which a moving subject, typically a coating jet, is imaged through filters, by means of which areas of different wavelength are distinguished from each other. The imaging speed is typically 25 images/second. Point-like subjects often become imaged as a stripe-like exposure.

The invention is intended to create a device for monitoring a web, by means of which faults in the web can be distinguished better than before, by directing the imaging power to where it is needed. The characteristic features of the present invention are stated in the accompanying claim 1.

The device for monitoring a web includes cameras imaging the web, for taking digital images from a transverse area of the web. The distance imaged by the device in the machine direction can be, for example, 80-300 mm. The term web refers to the webs in paper and coating machines. The term paper machine refers to paper and board machines. The term coating machine refers, in turn, to machines intended to coat paper or board. The web to be imaged by the device is essentially planar. In the device, each camera includes an imaging element, the individual pixels of which are real image-elements, and the real image-elements are combined to form effective image-elements in the machine direction of the web. By combining the real image-elements in the machine direction of the web, the desired shape of the effective image elements is obtained. In addition, the cameras used in the device are matrix cameras. The real image-elements, which are combined in the device to form effective image-elements, are exposed simultaneously. Thus, in the matrix camera pixels are simultaneously exposed, forming a two-dimensional matrix. The real image-elements are combined to form effective image-elements by exploiting the binning function of the matrix camera. The device includes a strobe-lighting unit, the synchronization of which is arranged with the imaging periods of the matrix cameras, to expose the image-elements simultaneously, the imaging periods being common to all the cameras. The image frequency is arranged to be such that essentially all the areas of the web are imaged, so that they can be processed as an essentially continuous image flow of the web.

By means of the device, the imaging power available in the matrix camera can be directed optimally in terms of detecting faults, by using a higher resolution in the critical direction and a lower resolution in the less direction. By selecting a suitable resolution for each purpose, unnecessary noise in the image signal can be avoided. The device is especially necessary in paper and coating machines, in which faults must be detected more accurately in the cross direction of the machine than in the machine direction. There is no benefit in imaging at as high a precision in the machine direction of a paper web as in the cross direction, as the limit to the precision in the machine direction is set by the speed of the machine and the exposure time used. Unlike in TDI cameras, if the cross-direction and machine-direction image-elements are simultaneously exposed in a matrix camera, the web is imaged as a continuous unified series of imaged areas. When the binning function in a matrix camera is utilized to combine real image-elements to form effective image-elements, the combination can be made using an application in the matrix camera itself. If the exposure is based on a light impulse produced by a strobe-lighting unit synchronized with the imaging frequency of the matrix cameras, the web area in the cross direction will be imaged simultaneously, even through there are several cameras in parallel. In exposures using strobe light, the real image-elements in the machine direction too will be exposed simultaneously.

Though the use of the apparatus will particularly reduce the bit flow, it will also improve the exposure and reduce noise. By means of the device, the amount of light is increased without lengthening the exposure time, which is very important when imaging high-speed webs. The device permits a more accurate transverse resolution than that permitted by devices according to the prior art at the same noise level. In other words, the device permits a reduction in the noise in the signal, caused by the micro-formation coming from the more accurate resolution.

In one embodiment, the pixels, i.e. real image-elements of the matrix camera are arranged to correspond to an area, with a side less than 0.5 mm long, preferably less than 0.3 mm long. When real image-elements of this size are combined to form effective image-elements in the machine direction of the web, the precision in the cross direction of the web will be at a level at which significant streaks can be detected. In the machine direction of the web, in turn, essential information will not be lost, as the dimensions of detectable faults in the web in the machine direction of the web are more than the area of the web recorded in the real image-element. In addition, by combining the real image-elements it is possible to reduce the occurrence of micro-formation.

In a second embodiment, the device includes processing means, a host unit, and a user interface for controlling the processing means and the host unit.

In a third embodiment, the processing unit belonging to the device is arranged to perform the analysis of images.

In a fourth embodiment, the device includes 1-7 cameras/m, preferably 2-5 cameras/m in the cross direction of the web. In that case, even a wide web can be imaged at the precision required to find machine-direction streaks, using a reasonably small number of cameras. In other words, if there are fewer cameras, the web cannot be imaged at the desired precision. On the other hand, if there are more cameras, the cost of the apparatus will be greater, without bringing any significant additional benefit.

In a fifth embodiment, the device is arranged to take images at an imaging frequency, which is more than 30 images/s, preferably more than 100 images/s. At such a high imaging frequency, even a high-speed web will move less than 5 mm, preferably less than 3 mm during the imaging period. The device is thus arranged to image a web, which travels typically at more than 400 m/min, preferably at even 2500 m/min.

In a sixth embodiment, the host unit belonging to the device is arranged to control the strobe-light unit and the timing of the matrix cameras. The use of the same host unit to control the strobe-light unit and the matrix cameras achieves a precise timing operation, allowing even a rapidly-moving web to be imaged with the precision required by the device, using several matrix cameras, the real image-elements contained in the imaging element of which are exposed simultaneously. In other words, when imaging high-speed webs, delays are significant. If the strobe-light unit and the matrix cameras' timing are controlled by the host unit, the detrimental effects of the delays will be reduced.

In a seventh embodiment, the binning function of the matrix cameras is used in such a way that the size of an effective image-element in the cross direction of the web is one real image-element. The number of cameras is minimized and the system is built at the most economical cost, as each real image-element is utilized in the cross-direction of the web as an effective image-element.

In an eighth embodiment, the size of an effective image-element in the cross direction of the web is 2-10, preferably 2-5 real image-elements. By combining the real image-elements in question in the machine direction of the web, no essential information will be lost, but a more rapid imaging frequency will be possible.

Figure 2:
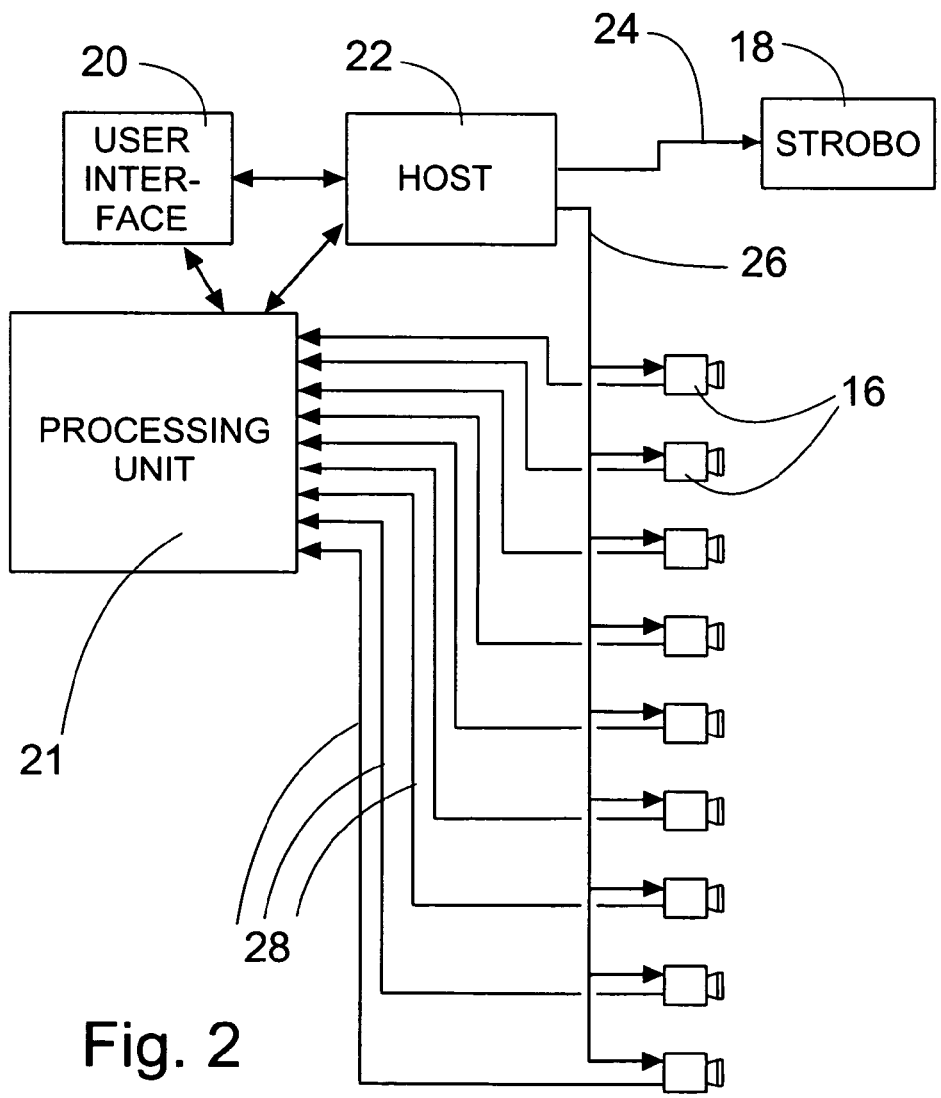
Figure 3A:
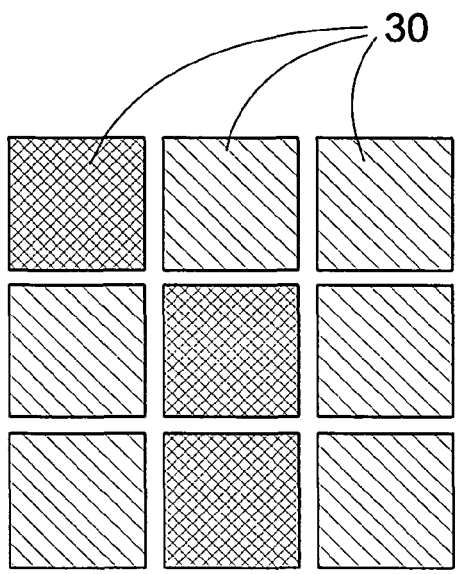
Figure 3B:
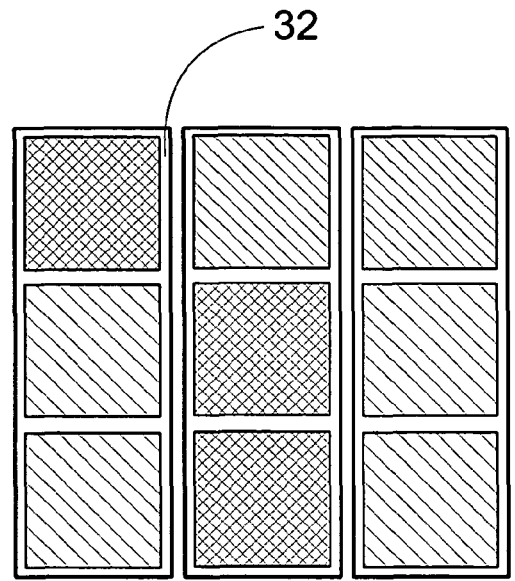
Figure 3C:
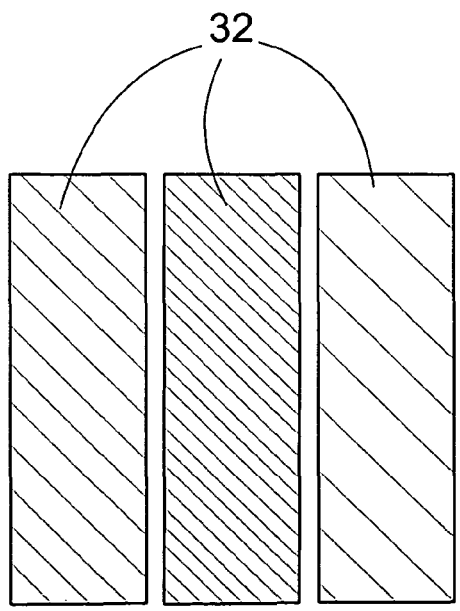
Figure 4:
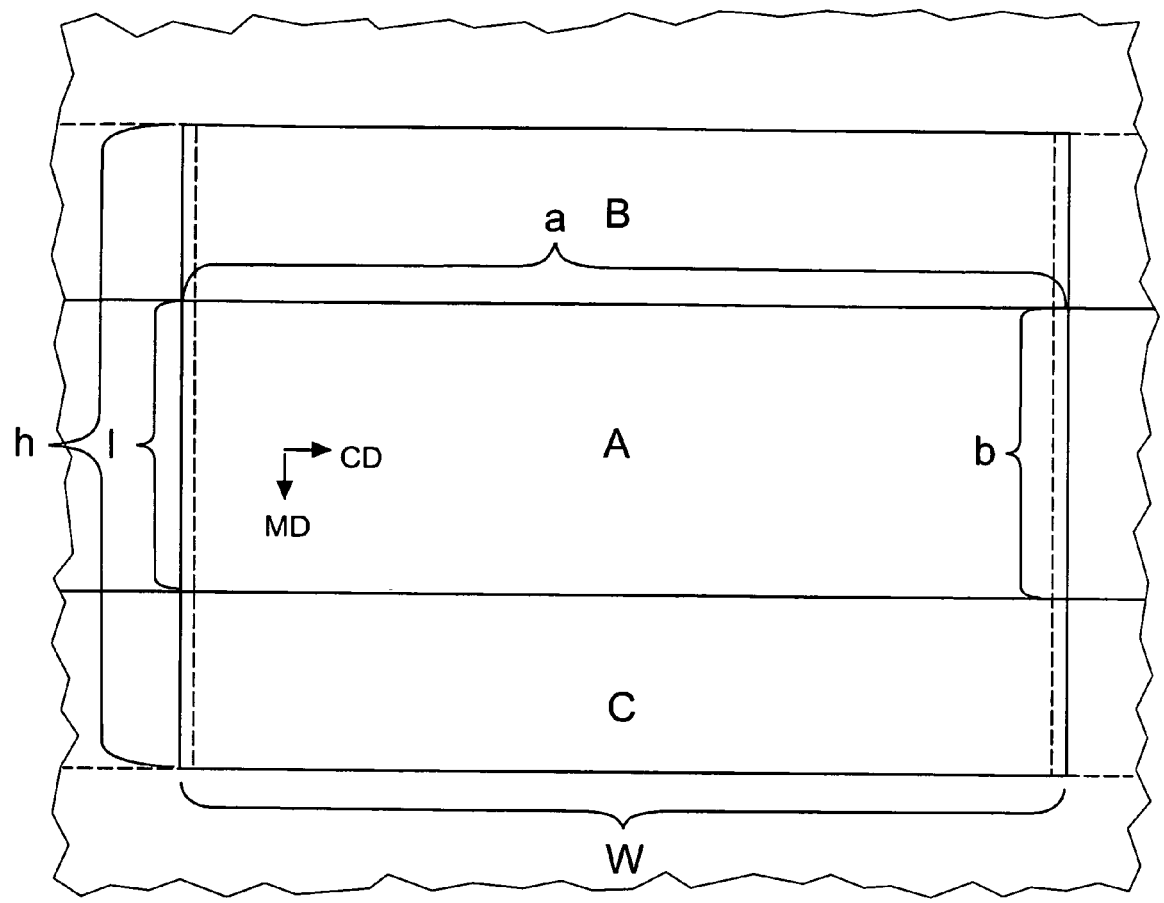
Figure 5:
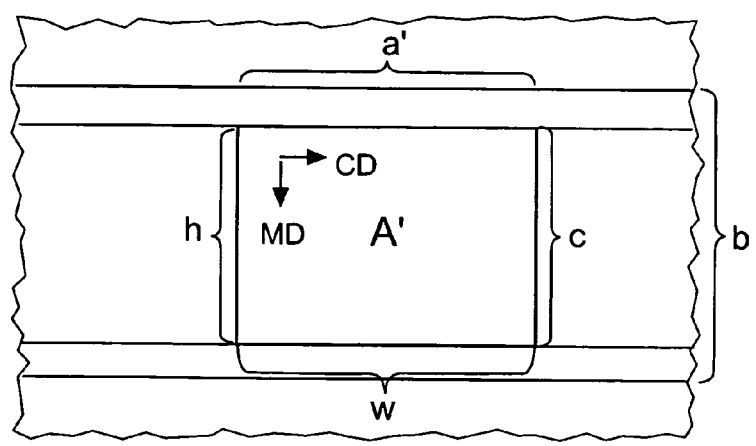

In the following, the invention is examined in detail reference to the accompanying drawings depicting some applications of the invention, in which FIG. 1 shows the device according to the invention in operation, FIG. 2 shows a diagram of the implementation of the device according to the invention, FIGS. 3a-3c show the device according to the invention for combining real image-elements to form effective image-elements, FIG. 4 shows the imaging area of a device used in the prior art, in which the imaging precision is 0.74 mm*0.74 mm, FIG. 5 shows the imaging area of the device according to the invention, in which the imaging precision is 0.50 mm*0.25 mm.

FIG. 1 shows the device according to the invention for monitoring a web. On the first side of the web 10 is a matrix-camera beam 12 for imaging the web. On the second side of the web is a strobe-lighting unit 14, for creating the correct exposure time and lighting level. The strobe-lighting unit can also be located on the same side of the web as the matrix-camera beam (not shown), in which case specified parts of the surface of the web can be examined in greater detail with the aid of reflected light. The matrix-camera beam 12 consists of the necessary number of matrix cameras 16, in which there is a binning function. The strobe-lighting unit 14 can advantageously be a strobe-lighting beam, which can, in turn be manufactured using many different methods, but one alternative that can be mentioned are LED lights 18.

In the device according to the invention, shown in FIG. 1, the matrix cameras 16 forming the matrix-camera beam 12 are CCD cameras. CCD cameras, achieve sufficient light power even with a short exposure time and thicker paper grades, as well as boards. In addition, with CCD cameras the image quality is sufficiently good.

The implementation of the device is explained as a diagram in FIG. 2. The processor means 21 and the host unit 22 are controlled through the user interface 20, which host unit in turn controls the operation of the strobe-lighting unit 14 and the matrix cameras 16. In one preferred embodiment, the host computer 22 first commands the cameras 16 to open the shutters (ERS=electronic rolling shutter). This followed by a standby time, when a check is made that the shutters of all the cameras 16 are open. After the standby time, the shutters of the cameras are sure to be open and the strobe-lighting unit 12 receives a command to light up for the desired period of time. When the strobe-lighting unit 12 is shut down after the desired time, the shutters of the cameras 16 still remain open for a standby time, after which they close and the data are read to the host computer 22. In reading, the voltages of the real image-elements exposed simultaneous by the imaging-elements forming the matrix are combined as desired using the binning function contained in the matrix cameras. The exposure time is adjusted as desired by varying the flash time of the strobe-lighting unit. In order to pass the lighting command, a bus 24 runs from the host unit 22 to the strobe-lighting unit 14 while a bus 26 runs to the matrix cameras 16 to transmit the imaging command. The data imaged using the matrix cameras 16 travels over the bus 28 to the processing unit 21, where the image is processed. The processing of the image can be performed, for example, by setting a threshold for the values of the image pixels. Preferably a single imaging command is enough for the cameras, on the basis of which the cameras are programmed to open the shutters and to close them after the desired period of time, as well as to read the image-elements from the imaging element by exploiting the binning function as desired to combine the real image-elements to form effective image-elements. The standby time is used to ensure that all the shutters of the cameras are open when the strobe-lighting unit flashes. In such a very high-speed system, in which up to hundreds of images are taken each second, delays easily become significant. Because of the disturbing effects of delays, standby times, which minimize the detrimental effects of the delays, are used. Significant delays appear in the signal transmitted to the cameras and in the operation of the cameras. The system described above is only one example of how the problems brought by delays can be solved and the flashes of the strobe-lighting unit synchronized with the operation of the cameras.

In connection with FIGS. 3-5, the invention is examined through the amount of the bit flow and by the limited nature of the bit flow being transferred from the camera. Besides the reduction in the bit flow made possible by the invention, it is important to take into account the advantage brought by the lighting made possible by the invention and the reduction in noise appearing in the signal. Though the advantage brought to the lighting by the binning function can be significant on machines manufacturing thick paper grades and boards, the essential feature in terms of the present invention is the reduction in the bit flow. The reduction in the bit flow being transferred from the matrix camera permits the matrix camera to be used in a mode in which the imaging frequency is considerably higher than when using a larger bit flow. The binning function of the matrix camera combines the real simultaneously exposed image-elements when reading them from the image-element. The binning function is implemented in an analog form, before the content of the real image-elements is converted into bits.

FIGS. 3a-3c show one possibility for converting the real image-elements 30 into effective image-elements 32. In FIG. 3a, one real image-element 30 is also an effective image-element 32. When the real image-elements 30 are combined to form effective image-elements 32, there are fewer effective image-elements 32. If three real image-elements 30 are combined to form a single effective image-element 32, and the number of real image-elements 30 is originally n, the number of effective image-elements 32 will be n/3. This should be taken into account when comparing FIGS. 3a and 3b. When the real image-elements 30 are combined, some information is lost, as the single value that was obtained when combining the real image-elements, is used as the value of the effective image-element after the combination. When the real image-elements 30 are combined using the binning function, the light power of the real image-elements are combined preferably in an analog manner. When the binning function is used, the effective image-elements 32 are lighter than the real image-elements, which is illustrated in FIG. 3c if it is compared with FIG. 3b.

FIG. 3a shows the real image-elements 30, i.e. the pixels simultaneously exposed by the matrix camera are arranged to correspond to an area, the length of the side of which is less than 0.5 mm, preferably less than 0.3 mm. In FIG. 3a, the real image-element 30 has a square shape and the sides of the real image-element are arranged to correspond to an area of the web with a side that is 0.5 mm. When the real image-elements are combined to form effective image-elements in the machine direction of the web, the cross-direction precision remains 0.5 mm. If three real image-elements in the machine direction of the web are combined to form an effective image-element, as is shown in FIG. 3b, the precision of the effective image-element in the machine direction of the web will be 1.5 mm. In that case, a single effective image-element will correspond to an area that is 0.5 mm in the cross direction of the web and 1.5 mm in the machine direction. At this precision, it is possible to take into account significant deviations in both directions. The significant deviations in the cross direction can be very narrow machine-direction streaks in the web.

Correspondingly, if the real image-elements are arranged to correspond to an area 0.3*0.3 mm, a single effective image-element will correspond to an area that is 0.3 mm in the cross direction of the web and 0.9 mm in the machine direction. At this precision, the detection of coating streaks appearing in the web will find all the coating streaks that are significant in terms of the process. In the machine direction of the web in turn, no essential information will be lost, as the dimensions of the faults that can be detected in the web in its machine direction are greater than the area of the web recorded in the real image-element. In addition, due to the machine-direction movement of the web during the exposure time, no essential information will be lost when the real image-element are combined in the machine direction. By combining the real image-elements, the appearance of micro-formation can also be reduced.

The real image-elements 30 shown in FIG. 3a are arranged to correspond to an area, with a side length of more than 0.05 mm, preferably more than 0.1 mm. Machine-direction stripes, which are significant in terms of web quality, are more than 0.05 mm, typically more than 0.1 mm wide. Thus there is no reason to image the web with greater precision. All in all, it can be said that the real image-elements are arranged to correspond to an area, the side of which in the web is 0.05-0.5 mm, preferably 0.1-0.3 mm.

The real image-elements can be arranged to correspond to even smaller areas, if the binning function is used in both directions. If more real image-elements are combined simultaneously in the machine direction of the web than in its cross direction, the same result as that above will be achieved. In other words, the cross-direction dimension of the effective image-elements being examined is 0.05-0.5 mm, preferably 0.1-0.3 mm while the machine-direction dimension is greater than the cross-direction dimension. This embodiment can be considered, for example, for use with imaging elements that are larger than at present. In addition, the embodiment in question permits the camera to be used in a mode, in which the imaging speed is made sufficiently high. The embodiment in question is also significant in terms of light power and micro-information. However, this embodiment requires more cameras, making the most advantageous cross-direction dimension of an effective image-element the cross-direction dimension of a real image-element. In other words, the binning function of the matrix camera is preferably used in such a way that the size of an effective image-element in the cross direction of the web is one real image-element.

In the machine direction, the effective image-element is less than 5 mm, preferably less than 3 mm. On the other hand, in the machine direction, the effective image-element is more than 0.3 mm, preferably more than 0.5 mm. The device in question is suitable for use in high-speed processes, in which in order to image the entire web more than 30, preferably more than 100 images are taken each second. At such a high imaging frequency, even a rapidly moving web will move a very short distance, which is less than 5 mm, preferably less than 3 mm, during an imaging period. On the other hand, during an imaging period the web will move more than 0.3 mm, preferably more than 0.5 mm. Therefore it will be desired to examine the web in greater detail in the cross direction than it is necessary in the machine direction, thus no essential information is lost when the machine-direction real image-elements are combined.

In the following example, the speed of the paper machine is 2100 m/min, i.e. 35 000 mm/s while the imaging should take place in a machine-direction area of less than 200 mm. A specific point in the paper will then travel the distance of 200 mm in 0.005714 seconds. If it is wished to image each point on the paper, 175 images should be taken each second. There can be imaging elements of different sizes available in the camera and the transfer speed of information from the camera can vary. FIGS. 4-5 and the calculations presented in connection with them are based on the assumption of using a matrix camera with an imaging element containing 800*600 pixels and a maximum of 38 million pixels that can be transferred from the camera each second. However, the invention is in no way bound to these cameras, but instead can be applied similarly with any matrix camera whatever, in which there is a function that combines image-elements. If the camera in question is used to take 175 images each second, each image can contain a maximum of about 217 000 pixels, due to the limitation of the size of the transfer channel, which limits the size of the image area being transferred.

The markings MD and CD appear in FIGS. 4 and 5, of which MD refers to the machine direction of the web and CD to the cross direction. FIG. 4 shows the imaging of the web using a matrix camera, the number of points of the imaging element of which in the cross direction of the web is marked by w, the numerical value of which in the example is 800, while there are 600 lines in the longitudinal direction h of the web. The imaging element of the camera sees the area A+B+C. The information contained in all the pixels of the imaging element cannot be transferred from the camera, if the imaging speed is too high. As stated above, the number of pixels to be trans-ferred according to a single image is limited and permits the imaging area size to be 800*271=216 800 pixels, i.e. 271 lines in the machine direction of the web. In this example, the information contained in the areas B and C is left unread. The information of the area A is read from the imaging element and then forwarded from the camera. Imaging in the machine direction should take place over a distance of 200 mm, which is marked by b. This distance consists of 271 points, so that the dimension of the side of a point will be 0.738 mm. An area 800*0.738 mm=590.4 mm wide, which is marked by a, can thus be detected in the cross direction. Much of the cross-direction material, i.e. 329 lines, is left unused. In the example in question, an area 590 mm wide can be imaged over a distance of 200 mm in the machine direction, using a single camera with a 800*600 imaging element. The precision of the imaging is 0.738 mm*0.738 mm. In order to monitor a 10-meter wide web, 17 cameras will then be required.

If it is desired to image more accurately, a single pixel should correspond to a smaller area of the web. When using the full width of the imaging element in the machine direction, the size of the readable image area in the machine direction is 800 points. The imaging in the machine direction should take place over a distance of 200 mm. This distance consists of 800 points, so that the dimension of the side of the point is 0.250 mm. Thus, in the width direction it is possible to detect an area with a width of 271*0.250 mm=67.75 mm. Much of the cross-direction material, i.e. 329 points, is left unused. By adding cameras so as to achieve a precision of 0.25*0.25 mm, an area 67.75 mm wide can be imaged over a distance of 200 mm using a single camera with an 800*600 imaging element. 149 cameras would then be required to monitor a 10-meter wide web. An imaging precision of 0.25 mm in the machine direction is unnecessarily accurate, as when the exposure time is, for example, 6 μs, the web will travel 0.21 mm during the exposure if the machine speed is 35 000 mm/s. As the smallest distinguishable area is 0.25 mm and its movement during the exposure time is 0.21 mm, practically no benefit is offered by a machine-direction precision of 0.25 mm. In the machine direction, the aforementioned precision of 0.75 mm will in addition be sufficient, because in the said direction the faults to be detected will generally be in that area. Extra precision will demand unnecessary transfer and processing power. The cameras imaging the web can be rotated through 90° as described above, but it is preferable for the width, i.e. the longer side, of the camera's imaging element to be parallel to the cross direction of the machine and the web.

FIG. 5 shows the imaging of a web using a matrix camera, the number of points of the imaging element of which in the trans-verse direction of the web is marked by w, the numerical value of which in the example is 800, with 600 lines in the longitudinal direction h of the web. The camera's imaging element sees the area A'.

As described above, the number of effective image-elements transferred during one second is limited. By using the binning function to combine three real image-elements to form one effective image-element, 800*200=160 000 effective image-elements will be forwarded from a camera equipped with an 800*600-image-element imaging element, covering the entire area of the imaging element in each image. If the bit flow being transferred from the camera in one second is limited to 38 million effective image-elements, it will be possible to take 237 images in one second. In the case in the example, the machine speed was 35 000 mm/s, so that the distance being imaged should be at least 148 mm. If the distance c being imaged is selected as 150 mm, a single real image-element will correspond to a square with a side of 0.25 mm. In the imaging element, there are 800 points in the cross direction of the web, which corresponds to 200 mm. In the example of FIG. 5, the area of the imaging element is exploited fully. In the example in question, a single camera with an 800*800 imaging element can be used to image an area with the width a'=200 mm over a distance of 150 mm in the machine direction. The precision of the imaging is 0.75 mm in the machine direction and 0.25 mm in the cross direction. 50 cameras will then be required to monitor a 10-meter wide web. This form of use described in connection with FIG. 5 is highly advantageous, as it exploits the entire area of the imaging element of the matrix camera and achieves a shorter 150-mm long imaging area in the machine direction. The imaging distance required in the machine direction has been advantageously shortened.

The example in the above description of FIGS. 4 and 5 gives only a single machine speed, exposure time, and size of imaging element. However, the invention can be correspondingly used even if the machine speed and exposure time vary over a wide range. The essential point is that no important information will be lost by combining machine-direction image-elements when reading the data from the imaging element. In addition, both an improved exposure result and reduced noise appearing in the signal, which leads to microformation appearing in accurate images, will be obtained. When three real image-elements are combined in the machine direction, the amount of data to be transferred will drop to one third, while retaining the cross-direction precision. If cameras with larger imaging elements than in the above description are used, the use of the binning function in both directions can be envisaged.

In order to reduce optical noise large pixels are preferable. In the accurate imaging of the web even the smallest differences in the texture of the paper will appear, thus increasing the micro-formation. Increased micro-formation will lead to increased signal noise. As the pixel size approaches zero, the noise will exponentially approach the maximum. As precision increases, the noise in the signal increases. The amount of noise can be reduced by combining the machine-direction real image-elements when reading them from the imaging element. In terms of minimizing noise, it is not worth using unnecessary precision in the machine direction, in which the preferable precision is 0.5-0.8 mm.

Besides reducing the bit flow, the use of the binning function also achieves other benefits. By making the optics more accurate, the imaging element is made to correspond to a smaller area than previously, so that the amount of light received by the imaging element will diminish. In seeking an improved precision, the darkness of the images may cause problems. When combining the real image-elements while reading data from the imaging element, the lighting of the images will increase, which will permit the use of shorter exposure times, or the imaging of thicker material using the same exposure time. Coating pigments absorb a great deal of light, making the increased amount of light very important. It is possible to obtain a greater lighting power for the effective image-elements and the entire image, because the real image-elements are combined to form effective image-elements, so that their light powers too are combined advantageously already before the bit flow is converted. The term conversion to a bit flow refers to A/D conversion.

The combination of the real image-elements to form effective image-elements takes place when the real image-elements are read from the imaging element, when the information contained in the real image-elements is combined. When the real image-elements are combined to form effective image-elements, the voltages are combined in an analog manner prior to conversion to a bit flow, i.e. A/D conversion.

The device for monitoring a web includes matrix cameras imaging the web, a strobe-lighting unit, a host unit, and a processing unit. The processing unit processes the images taken of the web into a form, in which the machine operator, the processing unit, or both analyse the images. The individual pixels of the imaging element of the matrix camera are real image-elements. Present matrix cameras include a function, by means of which these real image-elements can be combined. Using this function it is possible to combine the real image-elements already when they are still voltage differences in the imaging element. The combination of the real image-elements creates effective image-elements, which are converted into bits. By selecting the real image-elements as desired to be converted, the desired form of the effective image-elements is obtained. The method used in the combination is binning.

On a paper machine, narrow machine-direction streaks can appear especially in coated papers. To detect these streaks, a very precise resolution capacity is required in the cross direction of the web, but a high resolution in the machine direction will unnecessarily increase the noise appearing in the signal. Real image-elements are combined to form effective image-elements in the machine direction of the web, in order to reduce the bit flow. 2-10, preferably 2-5 real image-elements in the machine direction are combined to form an effective image-element. It is possible to envisage special applications, in which image-elements are combined in the cross direction. In these applications, an effective image-element would be 1-6, preferably 2-4 real image-elements. However, the binning function is preferably used in such a way that the size of the effective image-element in the cross direction is one real image-element.

The synchronization of the strobe light is made to correspond with the imaging period of the matrix cameras. All the matrix cameras have essentially the same imaging period. The timing of the strobe-lighting unit and the matrix cameras is controlled centrally by the host unit. The lighting of a desired point is performed in such a way that first the host unit commands the matrix cameras to open their shutters. After that, with a small delay the host unit commands the strobe-lighting unit to illuminate the area to be imaged. After that, the shutters of the matrix cameras are closed and the data is read from the imaging element. When the data is being read, the real image-elements are combined to form the desired effective image-element.

In a third embodiment, the distance imaged by the device in the machine direction is 80-300 mm, preferably 100-250 mm. If the speed of the paper machine is constant, the imaging frequency is set to be such that all the areas of the web are imaged, so that they can be shown as a continuous, or substantially continuous image of the web. In other words, all the areas of the web are imaged, so that they can be processed as a continuous or substantially continuous image flow of the web. The device according to the invention is suitable for use in high-speed processes, in which in order to image the entire web 30-200 images are taken each second, the area being imaged being the aforesaid 100-250 mm. On a high-speed paper machine, in which the speed of the paper is, for example, 2100 m/min, and the area to be imaged is 200 mm, 175 images should be taken each second, in order to create a continuous image of the entire web. On a slower board machine, in which the speed of the board is, for example, 400 m/min, and the area to be image is 200 mm, 33 images should be taken each second.

The invention claimed is:

1. Device for monitoring a moving web having a machine direction, the device comprising:
   matrix cameras for imaging the web in order to take digital images of the web from a transverse area of the web at an imaging frequency, each matrix camera having a binning function for combining voltages prior to an A/D conversion, and the imaging frequency being arranged for imaging essentially all the areas of the web, and
   a strobe-lighting unit synchronized with imaging periods of the matrix cameras, the imaging periods being common to all the matrix cameras for exposing imaging elements simultaneously
   wherein said image elements consist of pixels, and the individual pixels of the imaging elements of the cameras are real image-elements, which are arranged to be combined by said binning function to form effective image-elements of the web in the machine direction.

2. Device according to claim 1, characterized in that the pixels of the matrix camera are arranged to correspond essentially to a square area of the web, the length of the side of which area being less than 0.5 mm.

3. Device according to claim 1, characterized in that the device includes processing means, a host unit, and a user interface for controlling the processing means and the host unit.

4. Device according to claim 1, characterized in that the processing unit belonging to the device is arranged to perform the analysis of the images.

5. Device according to claim 4, characterized in that the processing unit is arranged to create thresholds for the values of the image pixels.

6. Device according to claim 1, characterized in that the device includes 1-7 matrix cameras per meter, in the cross direction of the web.

7. Device according to claim 1, characterized in that the device is arranged to take images at an imaging frequency, which is more than 30 images/s.

8. Device according to claim 3, characterized in that the host unit belonging to the device is arranged to control the timing of the strobe-lighting unit and the matrix cameras.

9. Device according to claim 1, characterized in that the distance imaged by the device in the machine direction of the web is 80-300 mm.

10. Device according to claim 1, characterized in that the binning function of the matrix camera is used in such a way that the size of an effective image-element, in the cross direction of the web, is one real image-element.

11. Device according to claim 1, characterized in that the size of an effective image-element, in the machine direction, is 2-10 real image-elements.

12. Device according to claim 1, characterized in that the matrix camera is a CCD camera.

13. Device according to claim 1, characterized in that the device includes 2-5 matrix cameras per meter, in the cross direction of the web.

14. Device according to claim 1, characterized in that the device is arranged to take images at an imaging frequency, which is more than 100 images/s.

15. Device according to claim 1, characterized in that the distance imaged by the device in the machine direction of the web is 100-250 mm.

16. Device according to claim 1, characterized in that the size of an effective image-element, in the machine direction, is 2-5 real image elements.

17. Device according to claim 1, characterized in that the pixels of the matrix camera are arranged to correspond essentially to a square area of the web, the length of the side of which area being less than 0.3 mm.

\* \* \* \* \*